United States Patent
de Poitiers et al.

(10) Patent No.: US 6,663,692 B2
(45) Date of Patent: Dec. 16, 2003

(54) PROCESS FOR PURIFYING CARBON DIOXIDE-CONTAINING GAS STREAMS

(75) Inventors: Keith de Poitiers, Fleet (GB); Sean Anthony Hennigan, Hull (GB)

(73) Assignee: BP Chemicals Limited, London (GB)

(*) Notice: Subject to any disclaimer, the term of this patent is extended or adjusted under 35 U.S.C. 154(b) by 109 days.

(21) Appl. No.: 09/931,189

(22) Filed: Aug. 17, 2001

(65) Prior Publication Data

US 2002/0020293 A1 Feb. 21, 2002

(30) Foreign Application Priority Data

Aug. 18, 2000 (GB) .............................................. 0020523

(51) Int. Cl.[7] .............................................. B01D 53/14
(52) U.S. Cl. .......................................... 95/237; 560/248
(58) Field of Search .......................... 95/237, 240, 239, 95/238; 560/245, 243, 248; 203/42

(56) References Cited

U.S. PATENT DOCUMENTS

| | | | | |
|---|---|---|---|---|
| 3,372,187 A | * | 3/1968 | Karnofsky | |
| 3,404,177 A | * | 10/1968 | Baba et al. | |
| 3,855,280 A | | 12/1974 | Severs, Jr. | |
| 3,948,621 A | * | 4/1976 | Cocuzza et al. | |
| 4,818,347 A | | 4/1989 | Roscher et al. | |
| 4,875,909 A | * | 10/1989 | Kakimoto et al. | |
| 5,066,365 A | * | 11/1991 | Roscher et al. | |
| 5,233,060 A | * | 8/1993 | Pendergast et al. | |
| 5,533,437 A | * | 7/1996 | Howard et al. | |
| 5,821,384 A | * | 10/1998 | Zoeller et al. | |
| 5,916,422 A | * | 6/1999 | Kimura et al. | |
| 6,040,474 A | * | 3/2000 | Jobson et al. | |
| 6,180,821 B1 | * | 1/2001 | Jobson et al. | |

FOREIGN PATENT DOCUMENTS

| | | |
|---|---|---|
| EP | 0 927 712 A1 | 7/1999 |
| EP | 0 985 657 A | 3/2000 |
| WO | WO 98/47851 A | 10/1998 |

OTHER PUBLICATIONS

Bedell, K., "Make VAM from ethylene," Hydrocarbon Processing: Petrochemical Develop, pp. 141–143 (1972).

* cited by examiner

Primary Examiner—Duane S. Smith
(74) Attorney, Agent, or Firm—Nixon & Vanderhye

(57) ABSTRACT

A process for removing at least one compound selected from acetic acid, acetate esters and aldehydes from a gaseous fraction comprising carbon dioxide and such a compound. The process includes the steps of (a) scrubbing in a scrubber at least part of the gaseous fraction with water and acetic acid to remove the acetic acid, acetate esters and/or aldehydes and (b) removing carbon dioxide from the scrubbed product of step (a) by absorption in aqueous potassium carbonate. The process may be used to remove acetate esters such as vinyl acetate and ethyl acetate and aldehydes such as acetaldehyde. The process may be employed in the manufacture of vinyl acetate by the reaction of ethylene, acetic acid and an oxygen-containing gas in the presence of a catalyst, or in the catalytic oxidation of (a) ethane and/or (b) ethylene to produce respectively (a) acetic acid and/or ethylene and (b) acetic acid.

11 Claims, 2 Drawing Sheets

PROCESS FOR PURIFYING CARBON DIOXIDE-CONTAINING GAS STREAMS

The present invention relates to a process for the removal of acetic acid and/or acetate esters and/or aldehydes from gaseous carbon dioxide streams containing one or more of these compounds and, in particular, the removal of such compounds from gaseous carbon dioxide streams produced in the manufacture of vinyl acetate from ethylene, acetic acid and an oxygen-containing gas and produced in the oxidation of ethane and/or ethylene.

BACKGROUND OF THE INVENTION

Generally, in the oxidation of olefins, such as the oxidation of ethane and/or ethylene to acetic acid, a gaseous fraction is produced which comprises the by-product carbon dioxide and also acetic acid. The carbon dioxide may be removed from the gaseous fraction by absorption in an aqueous potassium carbonate solution, desorbed by steam stripping and then vented to atmosphere. Prior to absorption, the acetic acid is generally removed from the carbon dioxide fraction by scrubbing. The gaseous fraction may also contain compounds which may not be removed by the scrubbing process and which may subsequently affect the efficiency of the carbon dioxide absorption step. Such compounds include acetates and aldehydes, for example, ethyl acetate, vinyl acetate and acetaldehyde.

Generally, in the manufacture of vinyl acetate, ethylene, acetic acid and an oxygen-containing gas are combined at elevated temperature in the presence of a catalyst. The gaseous product mixture may be cooled and quenched to produce a liquid fraction comprising vinyl acetate product and a gaseous fraction which may comprise unconverted oxygen, unconverted ethylene, carbon dioxide, small amounts of acetic acid and other compounds such as ethyl acetate and acetaldehyde. Typically, carbon dioxide is removed from the gaseous fraction by absorption in aqueous solutions of potassium carbonate. Generally, prior to carbon dioxide removal, acetic acid is removed from the gaseous fraction by scrubbing with an aqueous scrubbate. Such scrubbing and carbon dioxide removal processes are described in, for example, Hydrocarbon Processing, November 1972, pages 141–143 and EP-A-0 927 712.

U.S. Pat. No. 3,855,280 describes a process for the manufacture of vinyl acetate by reacting oxygen, ethylene and acetic acid in the presence of a Group VIII noble metal catalyst. The gaseous reaction product is separated into a liquid portion comprising the vinyl acetate product and a gas stream. The gas from the separator is scrubbed with water to recover additional vinyl acetate. The scrubbed gas stream is then scrubbed with a carbon dioxide-absorbing liquid to remove carbon dioxide.

U.S. Pat. No. 4,818,437 describes a process for isolating vinyl acetate from a gas mixture containing vinyl acetate, ethyl acetate, water and carbon dioxide formed in the reaction of ethylene with acetic acid and oxygen in the gas phase over catalysts containing palladium or palladium compounds. The gas mixture leaving the reaction zone is passed to a distillation column and the gas mixture leaving the top thereof is cooled. The gas which is not condensed during the cooling is washed with acetic acid in a washing column, to obtain an acetic acid solution containing vinyl acetate. A series of further distillations recovers pure vinyl acetate.

SUMMARY OF THE INVENTION

It has been observed that the efficiency of the carbon dioxide removal with aqueous potassium carbonate solution is reduced by the presence of potassium acetate in the system. Without wishing to be bound by any theory, it is thought that the formation of potassium acetate is due to the presence of acetate esters and/or aldehyde compounds in the gaseous fraction which, due to their limited solubility in water, are carried-over from the water scrubber and enter the carbon dioxide removal system. The presence of potassium acetate in the carbon dioxide removal system also leads to a need for a more frequent replacement of the potassium carbonate solution and hence also therefore to increased disruption of the process caused by more frequent emptying and refilling of the system with potassium carbonate solution.

It has now been found that the technical problems described above may be overcome or at least mitigated by scrubbing the carbon dioxide-containing gaseous fraction with an aqueous scrubbate comprising acetic acid in the scrubber prior to removing the carbon dioxide from the gaseous fraction.

Accordingly, the present invention provides a process for removing at least one compound selected from acetic acid, acetate esters and aldehydes from a gaseous fraction comprising carbon dioxide and said at least one compound, said process comprising the steps of (a) scrubbing in a scrubber at least part of the gaseous fraction to remove said at least one compound and (b) removing carbon dioxide from the scrubbed product of step (a) by absorption in aqueous potassium carbonate and in which process the gaseous fraction is scrubbed in said scrubber with water and acetic acid.

Treating the gaseous fraction with water and acetic acid reduces, when present, the quantity of acetate ester and/or aldehyde compounds fed to subsequent treatment stages such as the removal of carbon dioxide. However, total elimination of acetate esters and/or aldehyde compounds may not be achievable.

Beneficially, the reduction in acetate ester and/or aldehyde compounds achieved by the process of the present invention generally leads to increased efficiency in the subsequent removal of carbon dioxide by absorption in aqueous solutions of potassium carbonate. Typically, the amount of potassium carbonate used is reduced and more stable rates of production of vinyl acetate may be achieved due to less frequent replenishment of the potassium carbonate.

The process of the present invention may be used to remove one or more of acetic acid, acetate esters and/or aldehydes from gaseous streams comprising carbon dioxide produced, for example, in (i) the manufacture of vinyl acetate by the reaction of ethylene, acetic acid and an oxygen-containing gas in the presence of a catalyst or (ii) in the catalytic oxidation of (a) ethane and/or (b) ethylene to produce respectively (a) acetic acid and/or ethylene and (b) acetic acid.

A preferred embodiment of the present invention provides a process for the manufacture of vinyl acetate wherein ethylene, acetic acid and an oxygen-containing gas are combined in a reactor at elevated temperature in the presence of a catalyst which process comprises the steps of (a) withdrawing a gaseous stream from the reactor (b) cooling said gaseous stream to form (i) a liquid fraction comprising vinyl acetate and (ii) a gaseous fraction comprising carbon dioxide and at least compound selected from acetic acid, acetate esters and aldehydes (c) scrubbing in a scrubber at least part of said gaseous fraction to remove said at least one compound and (d) removing carbon dioxide from the scrubbed product of step (c) by absorption in aqueous potassium carbonate and in which process the gaseous fraction is scrubbed in said scrubber with water and acetic acid.

Vinyl acetate may be produced by combining ethylene, acetic acid and an oxygen-containing gas at elevated temperature in the presence of a catalyst using a process such as described in EP-A-0 569 924, EP-A-0 839 793, EP-A-0 672 453 and EP-A-0 685 449 the contents of which are herein incorporated by reference.

The catalyst suitably comprises a Group VIII metal and a promoter. Preferably, the catalyst further comprises a co-promoter. These compounds are suitably accommodated on a support.

With regards to the Group VIII metal, the preferred metal is palladium. The metal may be present in a concentration of greater than 0.2% by weight, preferably greater than 0.5% by weight, especially about 1% by weight based upon total weight of catalyst. The metal concentration may be as high as 10% by weight.

In addition to the Group VIII metal, the catalyst comprises a promoter. The promoter metal may be present in an amount of from 0.1 to 10% by weight in the finished catalyst.

The catalyst composition may comprise a co-promoter material. Suitable copromoters include Group I, Group II, lanthanide or transition metals, for example cadmium, barium, potassium, sodium, iron, manganese, nickel, antimony, and/or lanthanum, which are present in the finished catalyst as salts, e.g. an acetate salt. The preferred salts are potassium or sodium acetate.

The catalyst material is a supported catalyst. Suitable catalyst supports include porous silica, alumina, silica/alumina, silica/titania, titania, zirconia or carbon. Preferably the support is silica.

The process is carried out in a reactor and may suitably be operated at a temperature of from 100 to 400° C., preferably 140 to 210° C.

The process may be carried out in a fixed bed or fluid bed reactor.

The gases withdrawn from the reactor are subjected to cooling for example by using a heat exchanger and/or by quenching the gases by flowing counter to a flow of liquid acetic acid. Such cooling results in the formation of a liquid fraction comprising vinyl acetate product and a carbon dioxide-containing gaseous fraction which are separated. The liquid vinyl acetate fraction may be and is preferably purified, for example by distillation, to remove, for example, acetic acid.

In addition to carbon dioxide, the gaseous fraction may comprise unreacted ethylene, unreacted oxygen and small amounts of acetic acid, acetate ester and/or aldehyde compounds.

The acetate ester compounds present in the gaseous fraction, may include vinyl acetate and ethyl acetate, particularly, ethyl acetate.

The aldehyde compounds present may be, for example, acetaldehyde.

Typically, the gaseous fraction may comprise by weight, 0–5 wt % acetic acid, 0–2000 ppm vinyl acetate, for example, 0–500 ppm vinyl acetate, 0–2000 ppm ethyl acetate, for example, 0–500 ppm ethyl acetate and 0–5000 ppm acetaldehyde, for example, 0–750 ppm acetaldehyde.

At least part of the gaseous fraction is scrubbed in a scrubber with water and acetic acid to reduce the content of one or more of acetic acid, acetate ester and aldehyde compounds and, in particular to reduce the content of ethyl acetate and acetaldehyde.

Preferably, the acetic acid is added to the scrubber in liquid form.

The acetic acid may be fed to the scrubber as a mixture with the water, but preferably the acid is fed to the scrubber separately from the water. If the acetic acid is used as a mixture with the water, the acid may be pre-mixed or partly pre-mixed with the water prior to use.

The acetic acid may be, and is, preferably, fresh acid, that is, not recycled acetic acid.

Typically, the water is demineralised water.

The feed point of the acetic acid to the scrubber will depend on the concentration of acetate ester and/or aldehyde compounds present in the gaseous fraction to be scrubbed. Preferably, the acetic acid is fed to the scrubber at a point below the feed point of the water to the scrubber. Preferably, the acetic acid is fed into the lower half of the scrubber, such as approximately mid-way down the scrubber.

The quantity of acetic acid required will also depend on the concentration of acetate ester and aldehyde compounds present in the gaseous fraction. However, in general, the greater the concentration of acetate esters and aldehydes, the greater the quantity of acetic acid required.

Suitably, the ratio of acetic acid: water which may be used to scrub the gaseous fraction is 5–50:1, preferably, 15–35:1, such as 25:1 by volume.

Both the quantity of acetic acid required and the feed point to the scrubber may be determined by computer simulation and optimisation techniques.

Optionally, and preferably, prior to the scrubbing of the gaseous fraction with water and acetic acid, the gaseous fraction is treated with acetic acid in a scrubber to remove vinyl acetate.

Subsequently to scrubbing the gaseous fraction with water and acetic acid, the gaseous fraction may be contacted with an aqueous solution of potassium carbonate to absorb and remove carbon dioxide. The contacting may be carried any in any suitable apparatus, for example, an absorption column. A Benfield system may be, and is preferably, used.

The carbon dioxide may be desorbed from the potassium carbonate solution by any suitable means, for example, steam stripping. The desorbed carbon dioxide may be vented to atmosphere. The potassium carbonate solution may be recycled to an absorption column for reuse.

DETAILED DESCRIPTION OF THE DRAWINGS

The process of the present invention will now be illustrated with reference to FIG. 1 and the following Example.

DETAILED DESCRIPTION OF PREFERRED EMBODIMENTS

Figure 1:
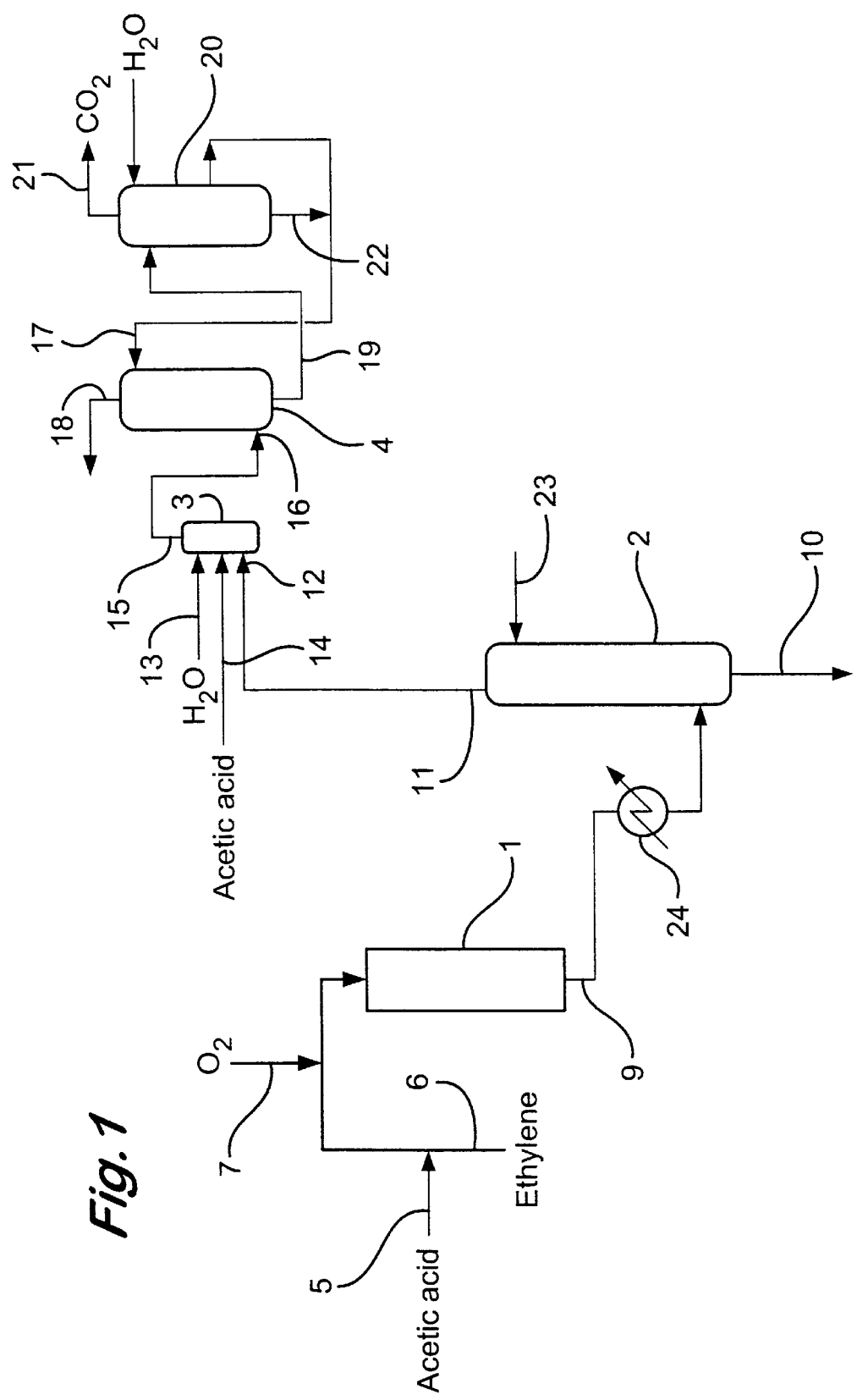
FIG. 1 is a schematic diagram of part of a vinyl acetate process.

In operation, acetic acid (5), oxygen (7) and ethylene (6) are fed into the reactor (1) containing a supported Group VIII noble metal catalyst. The gaseous products exit the reactor through exit (9) and are cooled by passing the gaseous products via a heat exchanger (24) to absorption column (2). In absorption column (2) the gaseous products are quenched with recycled acetic acid introduced via inlet (23). Liquid vinyl acetate together with liquid acetic acid exits from the bottom of the absorption column through exit (10) for further recovery and purification (not shown). A gaseous fraction comprising carbon dioxide, unreacted oxygen, unreacted ethylene, acetic acid and other compounds such as acetates and aldehydes exits the absorption column (2) via exit (11) and is fed into to scrubber (3) via inlet (12). Demineralised water is fed into the scrubber (3) via inlet (13). Fresh acetic acid is fed into the scrubber (3) via inlet (14). In the scrubber (3) the gaseous fraction is scrubbed to reduce the content of acetic acid, acetate and aldehyde compounds. The scrubbed gaseous fraction exits the scrubber (3) via exit (15) and is fed to absorption column (4) via inlet (16). In absorption column (4) carbon dioxide is removed from the scrubbed gaseous fraction by absorption in a potassium carbonate solution which is fed to absorption column (4) via inlet (17). The non-absorbed gases exit the absorption column (4) via exit (18) and may be recycled to absorption column (2) (not shown). The absorbed carbon dioxide is fed via exit (19) to a steam stripper (20) where the carbon dioxide is desorbed from the potassium carbonate solution and is vented to atmosphere via exit (21). The regenerated potassium carbonate solution is recycled via exit (22) to absorption column (4).

EXAMPLE

Using the apparatus such as described for FIG. 1 but with no acetic acid feed to the scrubber, the reactor was loaded with a silica supported palladium/gold catalyst. A solution of potassium acetate catalyst promoter was injected at the inlet of the reactor. The reactor was operated at 160° C. and 120 psig (8 barg). The total feed composition in mole % entering the catalyst bed was ethylene:oxygen:acetic acid:inerts 56:5:16:5.

The gases exiting from the reactor were passed to an absorption column operated at 7 barg and 30–40° C. and quenched with recycle acetic acid. The gaseous by-product was fed to the scrubber fed with 40 kg/hr quantity of water. The scrubbed gaseous fraction was passed to a Benfield carbon dioxide removal plant containing a potassium carbonate solution to remove carbon dioxide. The solution containing absorbed carbon dioxide was passed to a steam stripper where the carbon dioxide was desorbed and vented to atmosphere and the regenerated potassium carbonate solution recycled to the Benfield.

Periodically, samples of the condensate from the scrubber were taken and analysed. Analysis of the samples indicated that quantities of acetic acid, vinyl acetate, ethyl acetate and acetaldehyde were present.

Figure 2:
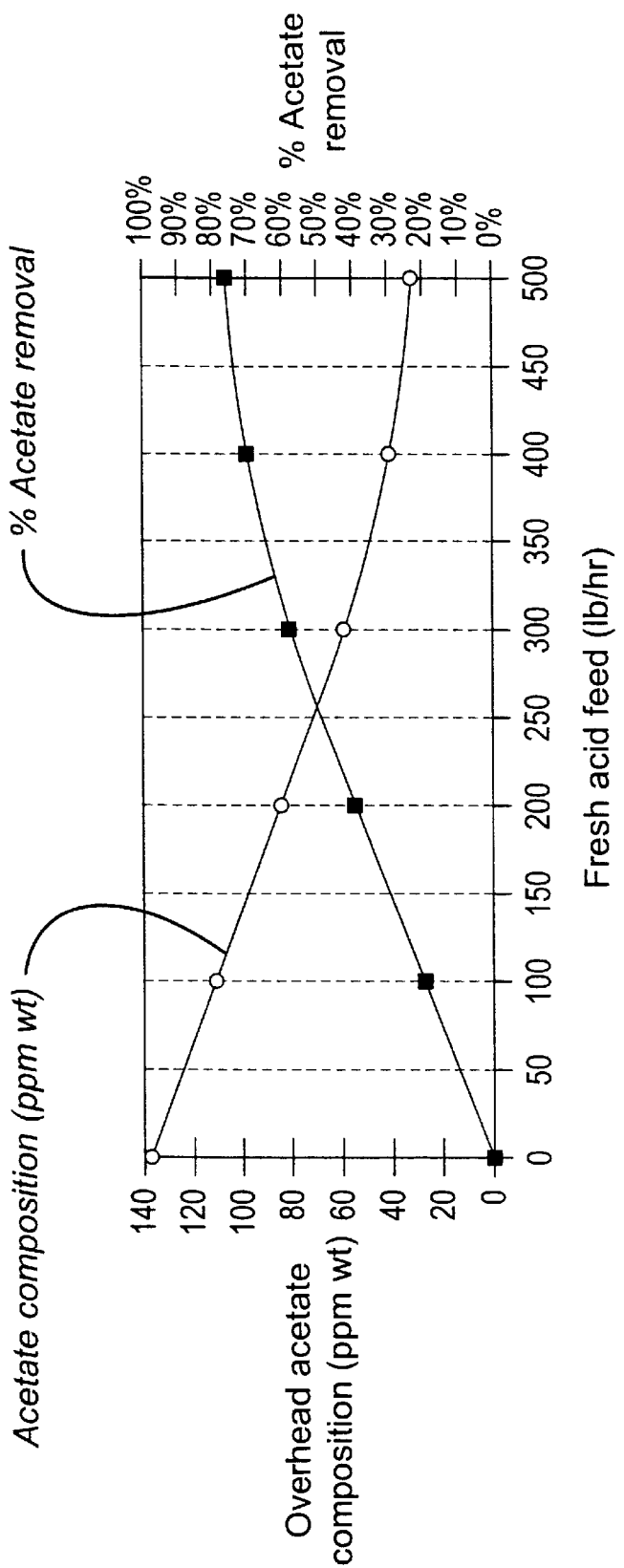
FIG. 2 is a graph showing the effect of adding fresh acetic acid to the scrubber on the concentration of acetate ester and/or aldehyde compounds as exemplified in the Example.

Computer simulation shows that for a constant water flow of 40 kg/hr into the scrubber, by varying the quantity of acetic acid added to the scrubber, the results as shown in FIG. 2 would be obtained.

Thus, as can be clearly seen from FIG. 2 the computer simulation shows the benefits of the present invention. The greater the quantity of acetic acid added to the scrubber, the greater the reduction in the acetate ester and/or aldehyde compounds in the gaseous fraction.

We claim:

1. A process for removing at least one compound selected from acetic acid, acetate esters and aldehydes from a gaseous fraction comprising carbon dioxide and said at least one compound, said process comprising the steps of (a) scrubbing in a scrubber at least part of the gaseous fraction to remove said at least one compound and (b) removing carbon dioxide from the scrubber product of step (a) by absorption in aqueous potassium carbonate and in which process the gaseous fraction is scrubbed in said scrubber with water and acetic acid.

2. A process for the manufacture of vinyl acetate wherein ethylene, acetic acid and an oxygen-containing gas are combined in a reactor at elevated temperature in the presence of a catalyst which process comprises the steps of (a) withdrawing a gaseous stream from the reactors, (b) cooling said gaseous stream to form (i) a liquid fraction comprising vinyl acetate and (ii) a gaseous fraction comprising carbon dioxide and at least one compound selected from acetic acid, acetate esters and aldehydes, (c) scrubbing in a scrubber at least part of said gaseous fraction to remove said at least one compound, and (d) removing carbon dioxide from the scrubber product of step (c) by absorption in aqueous potassium carbonate and in which process the gaseous fraction is scrubbed in said scrubber with water and acetic acid.

3. A process according to claim 1 wherein the at least one compound is selected from the group consisting of acetic acid, vinyl acetate, ethyl acetate and acetaldehyde.

4. A process according to claim 1 wherein the gaseous fraction comprises carbon dioxide, acetic acid, ethylene, oxygen and one or more compounds selected from the group consisting of acetate esters and aldehydes.

5. A process according to claim 1 wherein the gaseous fraction comprises by weight 0–5 wt % acetic acid, 0–2000 ppm vinyl acetate, 0–2000 ppm ethyl acetate and 0–5000 ppm acetaldehyde.

6. A process according to claim 1 wherein the acetic acid is fed to the scrubber separately from the water.

7. A process according to claim 1 wherein the acetic acid used in the scrubber is fresh acetic acid.

8. A process according to claim 6 wherein the acetic acid is fed to the scrubber at a point below the feed point of the water to the scrubber.

9. A process according to claim 8 wherein the acetic acid is fed into the lower half of the scrubber.

10. A process according to claim 1 wherein the ratio of acetic acid to water is 5–50 to 1 by volume.

11. A process according to claim 1 wherein prior to scrubbing the gaseous fraction, the gaseous fraction is treated with acetic acid in a scrubber to remove vinyl acetate.

* * * * *